US012606547B2

(12) United States Patent
Yang et al.

(10) Patent No.: US 12,606,547 B2
(45) Date of Patent: Apr. 21, 2026

(54) PREPARATION METHOD OF PHENYLISOXAZOLINE COMPOUND

(71) Applicants: SHENYANG SINOCHEM AGROCHEMICALS R&D CO., LTD., Shenyang (CN); JIANGSU YANGNONG CHEMICAL CO., LTD., Yangzhou (CN)

(72) Inventors: Jichun Yang, Shenyang (CN); Aiying Guan, Shenyang (CN); Qiao Wu, Shenyang (CN); Enming Wu, Shenyang (CN); Gongxin Wu, Shenyang (CN); Changling Liu, Shenyang (CN)

(73) Assignees: SHENYANG SINOCHEM AGROCHEMICALS R&D CO., LTD., Shenyang (CN); JIANGSU YANGNONG CHEMICAL CO., LTD., Yangzhou (CN)

( * ) Notice: Subject to any disclaimer, the term of this patent is extended or adjusted under 35 U.S.C. 154(b) by 622 days.

(21) Appl. No.: 18/003,906

(22) PCT Filed: Jun. 30, 2021

(86) PCT No.: PCT/CN2021/103472

§ 371 (c)(1),
(2) Date: Dec. 29, 2022

(87) PCT Pub. No.: WO2022/002116

PCT Pub. Date: Jan. 6, 2022

(65) Prior Publication Data

US 2023/0303545 A1 Sep. 28, 2023

(30) Foreign Application Priority Data

Jul. 2, 2020 (CN) ........................ 202010634286.4

(51) Int. Cl.
*C07D 413/10* (2006.01)
*C07D 239/54* (2006.01)

(52) U.S. Cl.
CPC ......... *C07D 413/10* (2013.01); *C07D 239/54* (2013.01)

(58) Field of Classification Search
CPC .................................................... C07D 413/10
(Continued)

(56) References Cited

FOREIGN PATENT DOCUMENTS

CN 105272973 A 1/2016
CN 105753853 A 7/2016
(Continued)

*Primary Examiner* — Taofiq A Solola
(74) *Attorney, Agent, or Firm* — NKL Law; Allen Xue

(57) ABSTRACT

In a synthesis method of a phenylisoxazoline compound 2-fluoro-4-chloro-5-methylaniline is used as starting material for firstly synthesizing a uracil ring, and then synthesizing an isooxazoline ring to obtain a target compound, phenylisoxazoline compound (VII), as shown in the reaction pathway below.

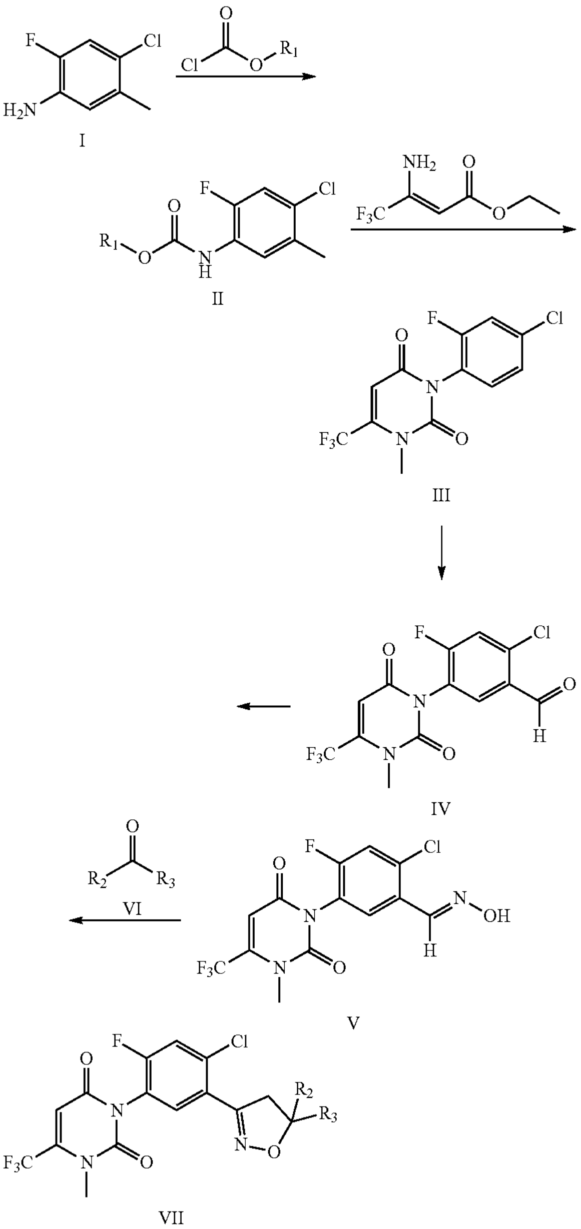

I, II, III, IV, V, VI, VII

The preparation method can be used for the synthesis of phenylisoxazoline containing uracil.

8 Claims, No Drawings

(58) Field of Classification Search
USPC .......................................................... 544/310
See application file for complete search history.

(56) References Cited

FOREIGN PATENT DOCUMENTS

| | | | | | |
|---|---|---|---|---|---|
| CN | 105777733 | A | | 7/2016 | |
| CN | 108570041 | A | | 9/2018 | |
| CN | 110818644 | A | | 2/2020 | |
| CN | 110818699 | A | | 2/2020 | |
| CN | 110964001 | A | | 4/2020 | |
| EA | 018521 | B1 | * | 8/2013 | ................ A61P 9/10 |
| KR | 100282153 | B1 | * | 2/2001 | |
| PT | 2344486 | E | * | 6/2013 | ................ A61P 9/06 |
| WO | WO-2014111871 | A1 | * | 2/2014 | .............. A61P 35/00 |
| WO | 2016095768 | A1 | | 6/2016 | |
| WO | 2019240082 | A1 | | 12/2019 | |

* cited by examiner

PREPARATION METHOD OF PHENYLISOXAZOLINE COMPOUND

TECHNICAL FIELD

The present invention belongs to the field of organic synthesis, in particular relates to a preparation method of a phenylisoxazoline compound.

BACKGROUND

Patent WO2016095768 has reported the phenylisoxazoline compound as shown in general formula I:

I

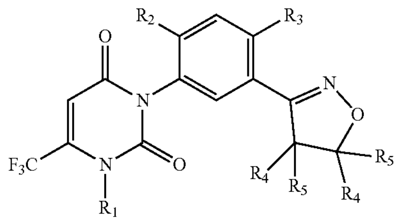

The compound of general formula I has good herbicidal activity, can effectively control *Echinochloa crusgalli, Setaria viridis, Cyperus difformis, Juncellus serotinus, Digitaria sanguinalis* (L.) Scop., *Arthraxon hispidus, Abutilon theophrasti, Zinnia elegans, Amaranthus retroflexus, Portulaca oleracea, Xanthium sibiricum, Solanum nigrum* L., *Cassia tora* Linn., *Hibiscus trionum* L., *Glycine soja* and other weeds, can obtain good weeding effect in low doses, and can be used as a herbicide in agriculture. Patents WO2016095768 and CN108570041 also involve the preparation of such compounds, but the compounds are synthesized by firstly synthesizing an isoxazoline ring and then synthesizing a uracil ring. The disadvantages of the above synthesis methods are: the stability of the isoxazoline ring synthesized firstly is not good; and the temperature and alkali requirements for the uracil cyclization are relatively harsh, which is easy to cause byproducts, resulting in long reaction time and low yield.

SUMMARY

The purpose of the present invention is to provide a preparation method of a phenylisoxazoline compound with cheap and available raw materials and simple synthesis process.

To realize the above purpose, the technical solution of the present invention is as follows:

A synthesis method of a phenylisoxazoline compound comprises:

1) using 2-fluoro-4-chloro-5-methylaniline and a chloroformate compound as raw materials to react for producing a carbamate compound;
2) reacting carbamate generated in step 1) with 3-amino-4,4,4-trifluorocrotonate, trifluoroamino crotonate followed by methylation with a methylating reagent to obtain uracil;
3) processing the uracil generated in step 2) by oxidization or dihalogenation hydrolysis to obtain uracil benzaldehyde;
4) reacting the uracil benzaldehyde (IV) generated in step 3) with hydroxylamine hydrochloride to obtain uracil benzaldoxime;
5) conducting NCS chlorination on the uracil benzaldoxime generated in step 4), followed by cyclization with an alkene compound to obtain the phenylisoxazoline compound.

A synthetic route is as follows:

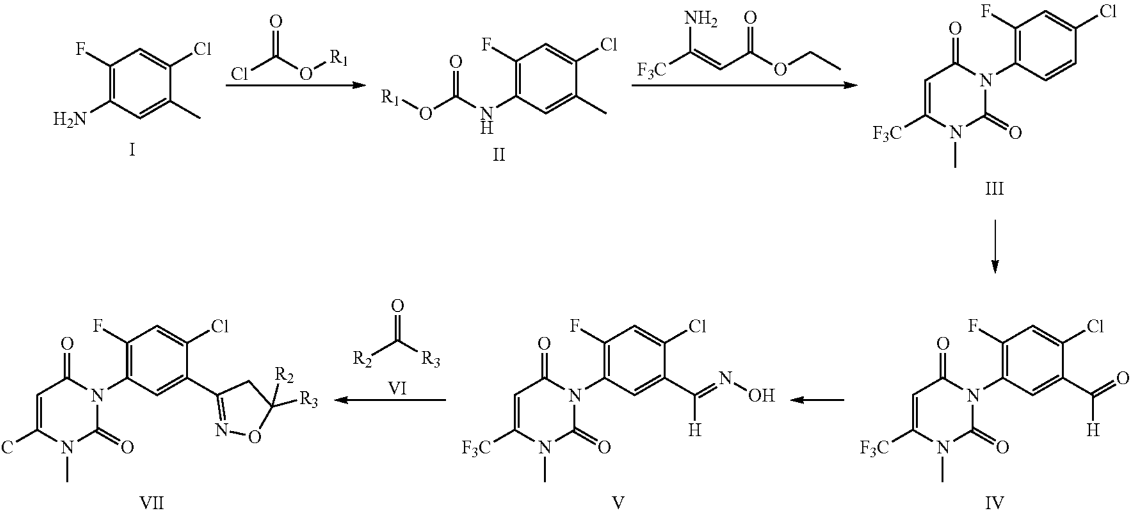

In the formula, $R_1$ is selected from methyl, ethyl, phenyl, 4-nitrophenyl or benzyl;

$R_2$ is selected from hydrogen, $C_1$-$C_4$ alkyl, $CO_2R_4$ or $CH_2OR_5$;

$R_3$ is selected from hydrogen, cyano, $C_1$-$C_4$ alkyl, $C_1$-$C_4$ haloalkyl, $CO_2R_4$ or $CH_2OR_5$;

$R_4$ is selected from hydrogen, $C_1$-$C_4$ alkyl, $C_1$-$C_4$ haloalkyl, $C_3$-$C_4$ alkenyl, $C_3$-$C_4$ alkyl, $C_1$-$C_4$ alkoxy $C_1$-$C_4$ alkyl, $C_1$-$C_4$ alkylcarbonyl oxy $C_2$-$C_3$ alkyl, and unsubstituted benzyl, unsubstituted furan methylene, unsubstituted tetrahydrofuran methylene, and substituted benzyl, furan methylene or tetrahydrofuran methylene by the following 1-4 groups independent substitutions: halogen, CN, $NO_2$, $C_1$-$C_4$ alkyl or $C_1$-$C_4$ haloalkyl;

$R_5$ is selected from hydrogen, $C_1$-$C_4$ alkyl, $C_1$-$C_4$ haloalkyl, $C_1$-$C_4$ alkoxy carbonyl, $C_1$-$C_4$ alkyl carbonyl, $C_1$-$C_4$ haloalkyl carbonyl, $C_3$-$C_6$ cycloalkyl carbonyl, $C_3$-$C_6$ halocycloalkyl carbonyl, $C_1$-$C_4$ alkyl sulfonyl, $C_1$-$C_4$ halo alkyl sulfonyl, $C_1$-$C_3$ alkyl aminosulfonyl, di($C_1$-$C_3$) alkyl aminosulfonyl, $C_1$-$C_3$ alkyl aminocarbonyl, di($C_1$-$C_3$) alkyl aminocarbonyl, di($C_1$-$C_3$)alkyl aminothiocarbonyl, $C_1$-$C_2$ alkylsulfuryl $C_2$-$C_4$ alkyl carbonyl, and phenyl $C_1$-$C_2$ alkyl, phenyl carbonyl, phenyl $C_1$-$C_2$ alkyl carbonyl, phenyl $C_2$-$C_4$ alkyl carbonyl, phenoxy $C_1$-$C_2$ alkyl carbonyl, thiophenyl carbonyl, pyrazole carbonyl and quinoline carbonyl which are unsubstituted or substituted by 1-4 groups independently substituted from the following groups; the following groups are halogen, CN, $NO_2$, $C_1$-$C_4$ alkyl, $C_1$-$C_4$haloalkyl, $C_1$-$C_4$ alkoxy, $C_1$-$C_4$ haloalkoxy, $C_1$-$C_4$ alkoxy carbonyl, $C_1$-$C_4$ alkyl, $C_1$-$C_4$ alkyl sulfonyl, or phenoxy which is independently substituted by 1-4 halogens, CN, $NO_2$, $C_1$-$C_4$ alkyl, $C_1$-$C_4$ haloalkyl, $C_1$-$C_4$ alkoxy or $C_1$-$C_4$ haloalkoxy.

Further, in general formulas II and VII, $R_1$ is selected from methyl, ethyl, phenyl, 4-nitrophenyl or benzyl;

$R_2$ is selected from hydrogen, $C_1$-$C_4$ alkyl, $CO_2R_4$ or $CH_2OR_5$;

$R_3$ is selected from hydrogen, $C_1$-$C_4$ alkyl or $C_1$-$C_4$ haloalkyl;

$R_4$ is selected from hydrogen, $C_1$-$C_4$ alkyl, $C_1$-$C_4$ haloalkyl, $C_3$-$C_4$ alkenyl, $C_3$-$C_4$ alkyl, $C_1$-$C_4$ alkoxy $C_1$-$C_4$ alkyl, $C_1$-$C_3$ alkylcarbonyl oxy $C_2$-$C_3$ alkyl, benzyl, furan methylene or tetrahydrofuran methylene;

$R_5$ is selected from hydrogen, $C_1$-$C_4$ alkyl, $C_1$-$C_4$ haloalkyl, $C_1$-$C_4$ alkoxy carbonyl, $C_1$-$C_4$ alkylcarbonyl, $C_1$-$C_4$ haloalkylcarbonyl, $C_3$-$C_6$ cycloalkyl carbonyl, $C_3$-$C_6$ halocycloalkyl carbonyl, $C_1$-$C_4$ alkyl sulfonyl, and $C_1$-$C_4$ haloalkyl sulfonyl.

Furthermore, in general formulas II and VII, $R_1$ is selected from methyl or ethyl;

$R_2$ is selected from hydrogen, $C_1$-$C_4$ alkyl, $CO_2R_4$ or $CH_2OR_5$;

$R_3$ is selected from hydrogen, $C_1$-$C_4$ alkyl or $C_1$-$C_4$ haloalkyl;

$R_4$ is selected from hydrogen, $C_1$-$C_4$ alkyl, $C_1$-$C_4$ haloalkyl, $C_3$-$C_4$ alkenyl, $C_3$-$C_4$ alkyl, $C_1$-$C_4$ alkoxy $C_1$-$C_4$ alkyl, $C_1$-$C_3$ alkylcarbonyl oxy $C_2$-$C_3$ alkyl, benzyl, furan methylene or tetrahydrofuran methylene;

$R_5$ is selected from hydrogen, $C_1$-$C_4$ alkylcarbonyl or $C_3$-$C_6$ cycloalkyl carbonyl.

Preferably, in general formulas II and VII, $R_1$ is selected from ethyl;

$R_2$ selected from hydrogen, cyanide, methyl, ethyl, n-propyl, n-butyl, isopropyl, isobutyl, tert-butyl, trifluoroethyl, trifluoromethyl or $CO_2R_4$;

$R_3$ is selected from hydrogen, methyl, ethyl, propyl, isopropyl, tert-butyl or trifluoromethyl;

$R_4$ is selected from hydrogen, methyl, ethyl, n-propyl, n-butyl, isopropyl, isobutyl, tert-butyl, trifluoroethyl, allyl, propargyl, methoxyethyl, ethoxyethyl, methyl carbonyloxyethyl, 2-tetrahydrofuran methylene or 3-tetrahydrofuran methylene.

Further, in step 1), 2-fluoro-4-chloro-5-methylaniline (I) is heated to 60-100° C. in a solvent and under alkaline conditions, and the chloroformate compound is dropwise added to react for 1-4 h to produce the carbamate compound (II), wherein the molar ratio of 2-fluoro-4-chloro-5-methylaniline (I), alkali and chloroformate compound is 1:(1-4):(1-2).

In step 2), the carbamate compound (II) obtained from step 1) reacts with 3-amino-4,4,4-trifluorocrotonate in the solvent and under alkaline conditions with a catalyst at 100-140° C. for 3-8 hours; Subsequently the temperature is reduced to room temperature, a methylation reagent is added and alkali is supplemented to react at 20-80° C. for 2-8 hours to obtain uracil (III).

Wherein the molar ratio of the carbamate (II), the 3-amino-4,4,4-trifluorocrotonate, the alkali, the catalyst and the methylation reagent is 1:(1-1.2):(1.5-3):(0.01-0.1):(1-2).

In step 3), the uracil (III) obtained in step 2), a halogenated reagent, the solvent and the catalyst are mixed to react at 50-150° C. for 2-10 hours; Subsequently the temperature is reduced to room temperature, and extraction is conducted to collect organic phase; vacuum distillation is conducted to obtain dihalide; acid is added for hydrolysis; the reaction is conducted at 50-100° C. for 4-12 hours; then vacuum distillation is conducted; the pH of the system is neutralized to be neutral; and the product is filtered to obtain uracil benzaldehyde (IV).

Wherein the molar ratio of the uracil (III), the halogenated reagent, the catalyst and the acid is 1:(2.5-3.5):(0.01-0.1):(10-30).

In step 4), the uracil benzaldehyde (IV) reacts with hydroxylamine hydrochloride in alcohol at room temperature for 1-6 hours, and the product is filtered to obtain uracil benzaldoxime (V), wherein the molar ratio of the uracil benzaldehyde (IV) to hydroxylamine hydrochloride is 1:(1-1.5).

In step 5), the uracil benzaldoxime (V) obtained in step 4) is added to the solvent; the halogenated reagent is added at 20-40° C., to react at this temperature for 1-2 hours; the temperature is reduced to 0-15° C., and the alkene compound (VI) and alkali are added at this temperature, to keep for 1-4 hours; the reactants are extracted and layered; and the organic phase is washed and then vacuum distilled to obtain the product phenylisoxazoline compound (VII);

wherein the molar ratio of the uracil benzaldoxime (V), the halogenated reagent, the alkene compound (VI) and the alkali is 1:(1-1.5): 1:(1-2).

The solvent in step 1) is selected from acetonitrile, tetrahydrofuran, 1,4-dioxane, ethylene glycol dimethyl ether, ethyl acetate, 2-butanone, N,N-dimethylformamide or dimethyl sulfoxide; the alkali is selected from potassium carbonate, sodium carbonate, potassium bicarbonate, sodium bicarbonate, sodium hydroxide, potassium hydroxide, lithium hydroxide, sodium tert-butoxide, potassium tert-butoxide, sodium ethoxide, sodium methoxide, triethylamine, pyridine or 4-dimethylaminopyridine.

Preferably, in step 1), the molar ratio of the 2-fluoro-4-chloro-5-methylaniline (I), the alkali and the chloroformate compound 1:(1.5-3):(1-1.5); the solvent is selected from acetonitrile, ethyl acetate or 2-butanone; and the alkali is selected from potassium carbonate, sodium carbonate, potassium bicarbonate or sodium bicarbonate;

The solvent in step 2) is selected from one or two of acetonitrile, tetrahydrofuran, 1,4-dioxane, ethylene glycol dimethyl ether, ethyl acetate, 2-butanone, N,N-dimethylformamide or dimethyl sulfoxide; the alkali environment and supplemented alkali are selected from potassium carbonate, sodium carbonate, potassium bicarbonate, sodium bicarbonate, sodium hydroxide, potassium hydroxide, lithium hydroxide, sodium tert-butoxide, potassium tert-butoxide, sodium ethoxide, sodium methoxide, triethylamine, pyridine or 4-dimethylaminopyridine; the catalyst is selected from one or two of a polyether phase transfer catalyst, a cyclic crown ether phase transfer catalyst, a quaternary ammonium salt phase transfer catalyst, a tertiary amine phase transfer catalyst, a quaternary ammonium base phase transfer catalyst and a quaternary phosphine phase transfer catalyst; and the methylation reagent is selected from iodomethane, dimethyl sulfate or chloromethane.

Preferably, in step 2), a rectification device can be used to separate the water and a low boiling point solvent in the reaction; the molar ratio of the carbamate (II), the trifluoroamino crotonate, the alkali is 1:(1-1.1):(1-2.5); the solvent is selected from one or two of acetonitrile, 2-butanone, N,N-dimethylformamide or dimethyl sulfoxide; the alkali environment and supplemented alkali are selected from potassium carbonate, sodium carbonate, potassium bicarbonate or sodium bicarbonate; and the catalyst is selected from one or two of PEG-200, PEG-400, PEG-600, 18-crown-6, 15-crown-5, cyclodextrin, benzyl triethylammonium chloride, tetrabutylammonium bromide, tetrabutylammonium chloride, tetrabutylammonium bisulfate, tetramethylammonium bromide, tributyl methyl ammonium chloride, trioctylammonium chloride, dodecyl trimethyl ammonium chloride, myristyl trimethyl ammonium chloride, pyridine, tributylamine, 1,8-diazodicyclodecundecan-7-ene (DBU) or triethylenediamine.

Further preferably, the catalyst in step 2) is selected from one or two of tetrabutylammonium bromide, tributyl methyl ammonium chloride or DBU.

In step 3), the halogenated reagent is selected from NBS, NCS, $Cl_2$ or $Br_2$; the solvent is selected from carbon tetrachloride, trichloromethane, acetonitrile, ethyl acetate, isopropyl acetate, tetrahydrofuran, 1,4-dioxane, ethylene glycol dimethyl ether or benzene; the catalyst is selected from azodiisobutyronitrile or benzoyl peroxide; the acid is selected from hydrochloric acid, sulfuric acid and formic acid; and the alkali is selected from sodium hydroxide, sodium carbonate, sodium bicarbonate, potassium hydroxide, potassium carbonate or potassium bicarbonate.

Preferably, in step 3), the halogenated reagent is selected from NBS; the solvent is selected from carbon tetrachloride or 1,4-dioxane; and the alkali is selected from sodium hydroxide or potassium hydroxide.

In step 4), the alcohol is selected from methanol, ethanol or isopropyl alcohol.

Preferably, in step 4), the reaction time is 1-3 hours.

In step 5), the reactants are extracted and layered, and the organic phase is washed with 1N hydrochloric acid and saturated salt successively; vacuum distillation is conducted to obtain the product phenylisoxazoline compound (VII); the halogenated reagent is selected from NBS, NCS, chlorine or bromide; the alkali is selected from sodium bicarbonate, potassium bicarbonate, sodium carbonate, potassium carbonate, triethylamine or pyridine; and the solvent is selected from one or two of dichloromethane, trichloromethane, ethylene glycol dimethyl ether, ethyl acetate or N,N-dimethylformamide;

Preferably, in step 5), the halogenated reagent is selected from NCS or bromate; and the alkali is selected from sodium bicarbonate, potassium bicarbonate or triethylamine.

In the preparation process, the content of the product is determined by high performance liquid chromatography with an external standard method.

In addition, the raw materials of chloroformate, 2-fluoro-4-chloro-5-methylaniline, 3-amino-4,4,4-trifluorocrotonate and the alkene compound (VI) used in the present invention are can be commercially available.

The present invention relates to an intermediate compound for synthesizing a phenylisoxazoline compound. The structural formula of the intermediate compound is shown in formula V of the reaction formula. The substituents are selected as described above.

The present invention further relates to the application of the compound in the synthesis of isoxazoline compounds containing uracil.

The present invention has the following advantages:

In the preparation method provided by the present invention, firstly the uracil ring is synthesized, and finally the isooxazoline ring is synthesized, without using expensive dichloromethylene dimethyl ammonium chloride. The raw materials used are readily available and the cost is low, which can effectively reduce the process cost. Moreover, the reactions involved in the method of the present invention are conventional operation units, which are simple in operation and easy in industrialization. In the reaction process, the related intermediates are stable and not easy to produce byproducts. In the reaction process, some intermediates do not need to be purified specially, and can be directly used in the next reaction, which is conducive to the continuous operation of industry. The yield is significantly higher than the prior art, and the total yield is increased by 3 times.

DETAILED DESCRIPTION

The following specific embodiments are used to further illustrate the present invention, but the present invention is not limited to these examples. The percentages involved in the following embodiments are mass percentages, such as content and purity.

Example 1 Synthesis of Intermediate V

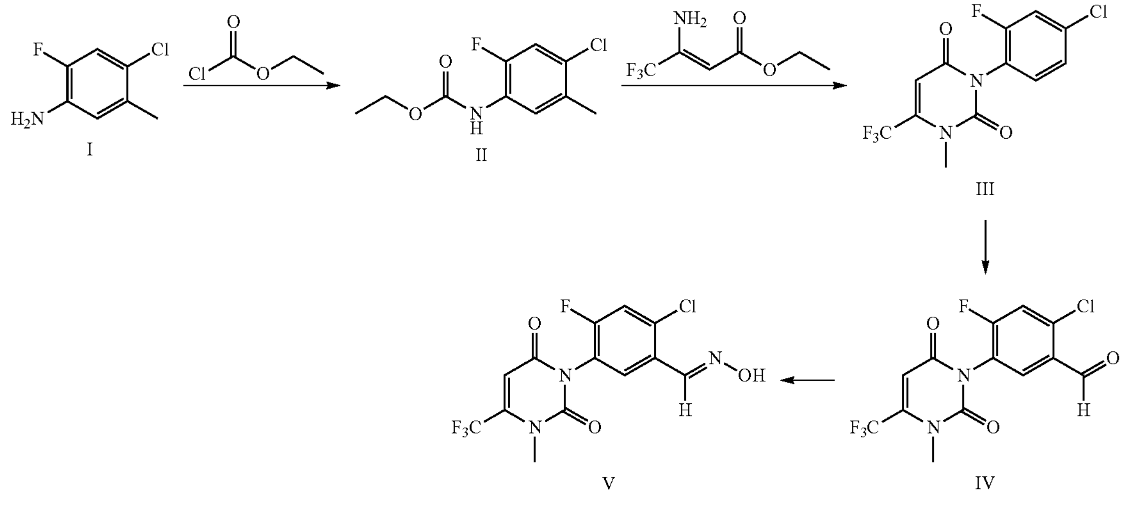

I II III IV V 63.8 g (0.4 mol) of 2-fluoro-4-chloro-5-methylaniline and 67.2 g (0.8 mol) of sodium bicarbonate were successively added to 300 ml of ethyl acetate, and heated to a micro-reflux state; 48.8 g (0.45 mol) of ethyl chloroformate was dropwise added, and reflux was maintained for 4 hours; the HPLC monitored that the reaction was completed, and the temperature was reduced to room temperature to add water; the product was extracted and layered; the organic phase was washed with saturated salt solution; the organic phase was dried by anhydrous magnesium sulfate; 94.2 g of intermediate II was obtained by desolvation under reduced pressure, which was oil with content of 98% (normalized by HPLC, the same below).

The above oil and 200 ml acetonitrile were added to a reaction flask containing 200 ml of DMF, 56.6 g (0.41 mol) of potassium carbonate, 75 g (0.41 mol) of ethyl 3-amino-4,4,4-trifluorocrotonate and 4.98 g (15.46 mmol) of tetrabutylammonium bromide and having a distillation column and a condenser. The temperature was increased to reflux and separate the low boiling point solvent; after 4 hours, the HPLC monitored that the reaction was completed; after cooling to room temperature, 56.6 g (0.41 mol) of potassium carbonate was supplemented, and 85.2 g (0.6 mol) of methane iodide was dropwise added, and stirred at room temperature for 6 hours; after the HPLC monitored that the reaction was completed, the reaction solution was slowly poured into water, stirred for 30 minutes, filtered and dried to obtain 128 g of intermediate III, which was light yellow solid with content of 97.8%, yield of 93% (measured by 2-fluoro-4-chloro-5-methylaniline) and melting point of 117-119° C.

68.8 g (0.2 mol) of II, 78.5 g (0.44 mol) of NBS, 3.5 g (21.3 mmol) of azodiisobutyronitrile and 300 ml of carbon tetrachloride were successively added into the reaction flask and heated to reflux reaction. After 2 hours, 11 g (0.06 mol) NBS and 0.5 g (3.05 mmol) of azodiisobutyronitrile were supplemented, and the reaction was continued for 2 hours; the HPLC monitored that the reaction was completed; the content of dibromide was 91.8% and the content of monobromide was 3.85%. The temperature was reduced to room temperature; 100 ml of 1N HCl was added to separate the organic phase; 200 ml of dichloromethane was added to the water phase to extract the organic phase; the organic phases were combined and concentrated under reduced pressure; Subsequently 150 ml of 88% formic acid was added, and the mixed solution was heated to reflux; the temperature was kept for 8 hours; the solvent was concentrated under reduced pressure, and carefully added to the water; the pH was adjusted to 9 with sodium hydroxide; the product was stirred for 15 minutes, filtered and dried to obtain 66.7 g of IV, which was light yellow solid, with content of 94.5%, yield of 89.9% and melting point of 176-177° C.

66.4 g (0.18 mol) of IV was added to 200 ml of ethanol and stirred at room temperature for 10 minutes; then a mixed solution of 14.4 g (0.207 mol) hydroxylamine hydrochloride and 50 ml of water was added, and stirred at room temperature to gradually form pale yellow turbid liquid. After reaction for 1 hour, the HPLC monitored that the reaction was completed, and the reaction was stopped. The product was stood, filtered, washed with 50 mL of water and dried to obtain 64.9 g of V, which was light yellow solid, with content of 96.1%, yield of 94.8%, and melting point of 182-185° C.

Based on 2-fluoro-4-chloro-5-methylaniline, the yield was 79.3%.

Example 2 Synthesis of Compound VII-1

0.76 g (2 mmol) of uracil benzaldoxime (V) was dissolved in 20 ml of dichloromethane and 5 ml of N,N-dimethylformamide. The temperature was increased to 35° C., and 0.28 g (2.1 mmol) of NCS was carefully added at the temperature, and the reaction was maintained at this temperature for 1 hour. The temperature was reduced to 0-5° C.; the mixed solution of 0.23 g (2 mmol) of ethyl methacrylate, 0.22 g (2.2 mmol) of triethylamine and 5 ml of methylene chloride was dropwise added; the reaction was conducted at the temperature for 1.5 h; after the HPLC monitored that the reaction was completed, the product was washed with 1N hydrochloric acid, water and saturated salt successively, and the organic phase was dried with anhydrous magnesium sulfate and desolventized to obtain 0.81 g of light yellow oil, with content of 96.7% and yield of 81.7%. $^1$H-NMR (300 MHz, internal standard TMS, solvent $CDCl_3$) δ(ppm): 1.35 (t, 3H), 1.68 (s, 3H), 3.38 (d, 1H), 3.60 (s, 3H), 3.90 (d, 1H), 4.30 (m, 2H), 6.25 (s, 1H), 7.38 (d, 1H), 7.79 (d, 1H).

Based on 2-fluoro-4-chloro-5-methylaniline, the total yield was 64.8%.

Reference embodiment 1 Preparation of compound VII-1 (WO2016095768)

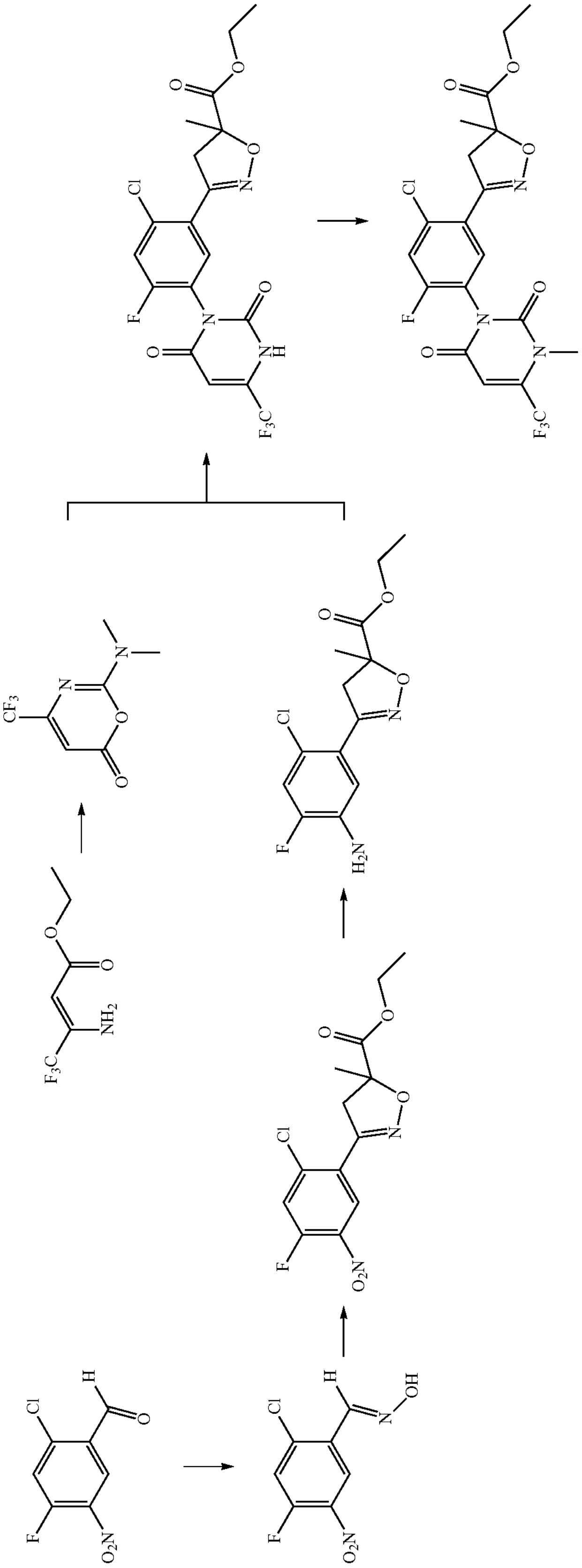
Compound VII-1

1) Preparation of 2-chloro-4-fluoro-5-nitrobenzaldoxime 42 g (0.206 mol) of 2-chloro-4-fluoro-5-nitrobenzaldehyde was dissolved in 200 ml of ethanol, reduced to 0° C., and 17.4 g (0.25 mol) of hydroxylamine hydrochloride aqueous solution was added under stirring; and then the temperature was raised to room temperature for stirring reaction. After 2 hours, TLC monitored that the reaction was completed. The solution was poured into water, and filtered to obtain 38.3 g (98%) of white solid, with yield of 83.4%.

2) Preparation of 3-(2-chloro-4-fluoro-5-nitrophenyl)-5-methyl-4,5-dihydroisooxazol-5-ethyl carboxylate 43.7 g (0.2 mol) of 2-chloro-4-fluoro-5-nitrobenzaldoxime was dissolved in 150 ml of N,N-dimethylformamide and heated to 30° C.; and 32 g (0.24 mol) of NCS was added in batches at this temperature to form a light yellow solution, and the reaction was kept at 35° C. for 1 hour. The temperature was reduced to room temperature; 300 ml of dichloromethane was added; then the solution was washed twice with 1N hydrochloric acid, washed with saturated salt twice, dried with anhydrous magnesium sulfate and suction-filtered; the dichloromethane solution was reduced to 0-5° C., and a mixed solution of 34.2 g (0.3 mol) of ethyl methacrylate and 31 g (0.3 mol) of triethylamine was dropwise added, and the reaction was maintained at the temperature for 1 hour. The solution was washed successively with 1N hydrochloric acid and saturated salt; the organic phase was dried with anhydrous magnesium sulfate; and after desolvation, column chromatography (ethyl acetate:petroleum ether=1:3) was conducted to obtain 57 g (97%) of light yellow solid, with yield of 83.6%.

3) Preparation of 3-(2-chloro-4-fluoro-5-aminophenyl)-5-methyl-4,5-dihydroisooxazol-5-ethyl carboxylate 57 g (0.18 mol) of 3-(2-chloro-4-fluoro-5-nitrophenyl)-5-methyl-4,5-dihydroisooxazol-5-ethyl carboxylate was dissolved in 300 ml of ethyl acetate, and 163 g (0.72 mol) of stannous chloride dihydrate was added in batches under heating, and then the reaction was conducted under reflux for 8 hours. The TLC monitored that the reaction was completed. The solution was cooled to room temperature, added to ice water, adjusted with sodium hydroxide until pH was 8, extracted with ethyl acetate, washed with saturated salt, dried with anhydrous magnesium sulfate and then distilled under reduced pressure to obtain 31 g of oil, which was directly used for the next reaction without purification, with content of 90% and yield of 51.6%.

4) Preparation of 2-dimethylamino-4-trifluoromethyl-6H-1,3-oxazine-6-one 25 g (0.15 mol) of dichloromethylene dimethyl ammonium chloride was added to 100 ml of chloroform, and heated to 60° C.; a mixed solution of 25 g (0.14 mol) of 3-amino-4,4,4-trifluorocrotonate and 15 ml of chloroform was dropwise added; the reflux reaction was continued; the solution was gradually changed from pale yellow turbid to clear; and after 4 hours, the TLC monitored that the reaction was completed. The solution was cooled to room temperature; saturated sodium bicarbonate aqueous solution was added; the organic phase was separated; the solution was washed with saturated salt; the organic phase was dried with anhydrous magnesium sulfate, and distilled under reduced pressure to obtain 30.8 g of light yellow solid.

5) Preparation of 3-(2-chloro-5-(2,6-dioxy-4-trifluoromethyl-3,6-dihydropyrimidine-1(2H)-yl)-4-fluorophenyl)-5-methyl-4,5-dihydroisooxazol-5-ethyl carboxylate 13.2 g (0.046 mol) of 3-(2-chloro-4-fluoro-5-aminophenyl)-5-methyl-4,5-dihydroisooxazol-5-ethyl carboxylate and 9.8 g (0.047 mol) of 2-dimethylamino-4-trifluoromethyl-6H-1,3-oxazine-6-one were added successively to a reaction flask containing 100 ml of acetic acid; the temperature was raised to reflux reaction to form a dark solution; and the reaction was conducted at this temperature for 6 h, and the solvent was evaporated under reduced pressure; the sodium bicarbonate aqueous solution was added to adjust the pH to 7; the solution was extracted with ethyl acetate and dried with anhydrous magnesium sulfate; and the solvent was evaporated under reduced pressure to obtain crude product; and the crude product was recrystallized with ethanol to obtain 14.5 g (95%) of white solid, with yield of 64.6%.

6) Preparation of Compound VII-1

14 g (0.031 mol) of 3-(2-chloro-5-(2,6-dioxy-4-trifluoromethyl-3,6-dihydropyrimidine-1(2H)-yl)-4-fluorophenyl)-5-methyl-4,5-dihydroisooxazol-5-ethyl carboxylate and 12.9 g (0.094 mol) of potassium carbonate were successively added to the reaction flask with 150 ml of N,N-dimethylformamide, and cooled to 0° C.; 8.9 g (0.062 mol) of iodomethane was dropwise added, and then the temperature was increased to room temperature for stirring reaction for 6 h. The TLC monitored that the reaction was completed. The solution was poured into water, extracted with ethyl acetate, and washed with saturated salt; the organic phase was dried with anhydrous magnesium sulfate, distilled under reduced pressure, and subjected to column chromatography (ethyl acetate:petroleum ether=1:5) to obtain 13.2 g of oil (94%), with yield of 83.8%.

Based on 2-chloro-4-fluoro-5-nitrobenzaldehyde, the total yield was 19.5%.

In accordance with the methods described in embodiments 1 and 2 above, ethyl methacrylate in synthesis embodiment 2 was replaced with methyl methacrylate, isopropyl methacrylate, n-butyl methacrylate, n-propyl methacrylate, tert-butyl methacrylate, 2-ethoxy ethyl methacrylate, 2-(trifluoromethyl) methyl acrylate, ethyl acrylate, 2-methyl-1-heptene, and 2,4-dimethyl-1-pentene to prepare compounds belonging to formula VII, other than compound VII-1. Specific nuclear magnetic data and yields of compounds shown in formula VII are shown in Table 1:

TABLE 1
| No. | Structure | Nuclear magnetic data ($^1$HNMR, 300 MHz, internal standard TMS, solvent $CDCl_3$) | Yield: Based on uracil benzaldoxime (V) | Yield: Based on 2-fluoro-4-chloro-5-methyl-aniline |
|---|---|---|---|---|
| VII-2 | 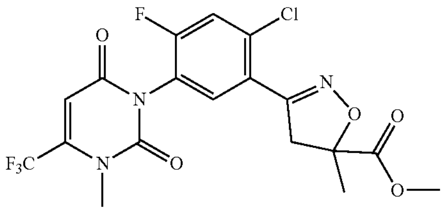 [SMILES: COC(=O)C1(C)CC(c2cc(-n3c(=O)cc(C(F)(F)F)n(C)c3=O)c(F)cc2Cl)=NO1] | 1.70 (s, 3H), 3.38 (d, 1H), 3.56 (s, 3H), 3.99 (d, 1H), 4.32 (s, 3H), 6.36 (s, 1H), 7.36 (d, 1H), 7.69 (d, 1H) | 85.2% | 67.6% |
| VII-3 | 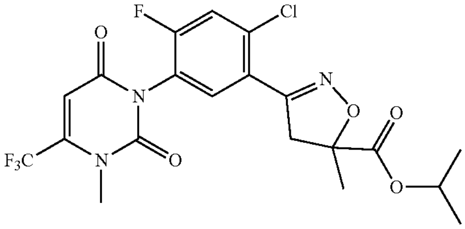 [SMILES: CC(C)OC(=O)C1(C)CC(c2cc(-n3c(=O)cc(C(F)(F)F)n(C)c3=O)c(F)cc2Cl)=NO1] | 1.25 (m, 6H), 1.69 (s, 3H), 3.37 (m, 1H), 3.56 (s, 3H), 3.93 (m, 1H), 5.07 (m, 1H), 6.36 (s, 1H), 7.37 (d, 1H), 7.68 (d, 1H) | 78.2% | 62% |
| VII-4 | 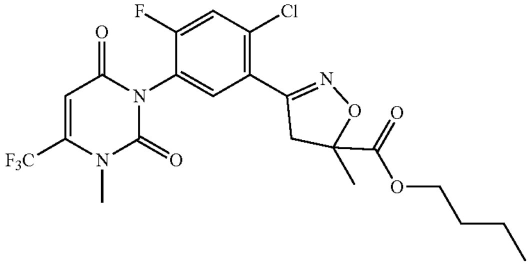 [SMILES: CCCCOC(=O)C1(C)CC(c2cc(-n3c(=O)cc(C(F)(F)F)n(C)c3=O)c(F)cc2Cl)=NO1] | 0.94 (3H, t), 38 (4H, m), 1.71 (3H, s), 3.37 (1H, d), 3.55 (3H, s), 3.99 (1H, d), 4.21 (2H, t), 6.36 (1H, s), 7.35 (1H, d), 7.68 (1H, d) | 75% | 59.5% |
| VII-5 | 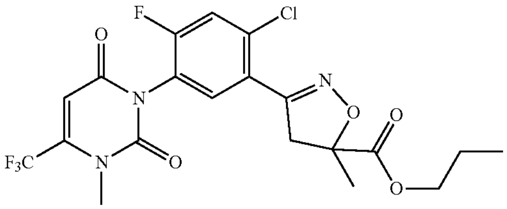 [SMILES: CCCOC(=O)C1(C)CC(c2cc(-n3c(=O)cc(C(F)(F)F)n(C)c3=O)c(F)cc2Cl)=NO1] | 0.96 (3H, t), 1.76-1.67 (5H, m), 3.38 (1H, d), 3.56 (3H, s), 4.01 (1H, d), 4.17 (2H, t), 6.36 (1H, s), 7.35 (1H, d), 7.62 (1H, d) | 72.6% | 57.6% |
| VII-6 | 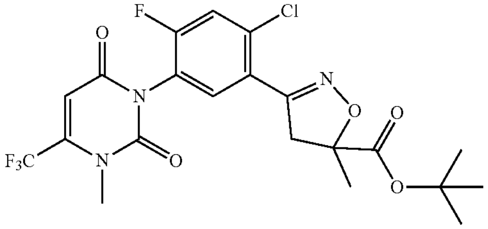 [SMILES: Cn1c(C(F)(F)F)cc(=O)n(-c2cc(C3=NOC(C)(C(=O)OC(C)(C)C)C3)c(Cl)cc2F)c1=O] | 1.50 (9H, s), 1.66 (3H, s), 3.32 (1H, d), 3.56 (3H, s), 3.96 (1H, d), 6.36 (1H, s), 7.35 (1H, d), 7.66 (1H, d) | 76% | 60.3% |
| VII-7 | 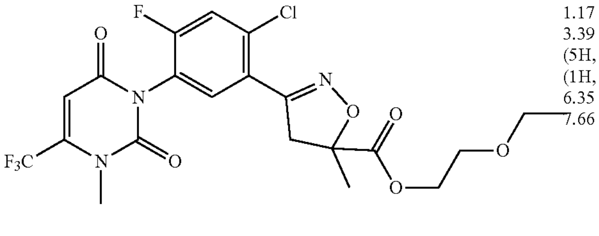 | 1.17 (3H, t), 1.71 (3H, s), 3.39 (1H, d), 3.56-3.46 (5H, m), 3.66 (2H, q), 4.01 (1H, d), 4.41-4.28 (2H, m), 6.35 (1H, s), 7.34 (1H, d), 7.66 (1H, d) | 69% | 54.7% |

TABLE 1-continued

| No. | Structure | Nuclear magnetic data ($^1$HNMR, 300 MHz, internal standard TMS, solvent $CDCl_3$) | Yield: Based on uracil benzal-doxime (V) | Yield: Based on 2-fluoro-4-chloro-5-methyl-aniline |
|---|---|---|---|---|
| VII-8 | 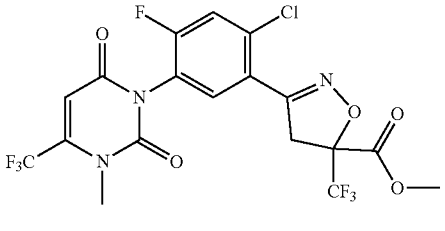 [SMILES: COC(=O)C1(C(F)(F)F)CC(c2cc(-n3c(=O)cc(C(F)(F)F)n(C)c3=O)c(F)cc2Cl)=NO1] | 3.56 (3H, s), 3.93 (3H, s), 3.98 (1H, d), 4.16 (1H, d), 6.37 (1H, s), 7.39 (1H, d), 7.70 (1H, d) | 73% | 57.9% |
| VII-9 | 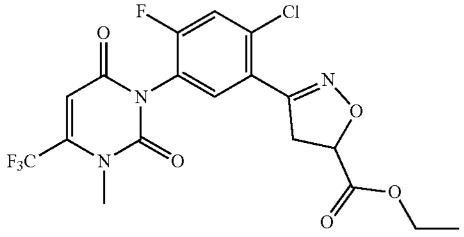 [SMILES: CCOC(=O)C1CC(c2cc(-n3c(=O)cc(C(F)(F)F)n(C)c3=O)c(F)cc2Cl)=NO1] | 1.33 (3H, t), 3.56 (3H, s), 3.79 (2H, m), 4.28 (2H, q), 5.18 (1H, m), 6.36 (1H, s), 7.37 (1H, d), 7.69 (1H, d) | 87.2% | 69.1% |
| VII-10 | 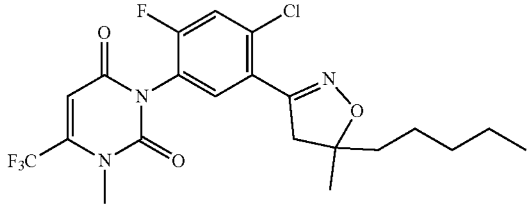 [SMILES: CCCCCC1(C)CC(c2cc(-n3c(=O)cc(C(F)(F)F)n(C)c3=O)c(F)cc2Cl)=NO1] | 0.90 (3H, t), 1.32 (6H, m), 1.43 (3H, d), 1.71 (2H, m), 3.15 (1H, m), 3.31 (1H, m), 3.56 (3H, s), 6.36 (1H, s), 7.33 (1H, d), 7.64 (1H, dd) | 72.5% | 57.5% |
| VII-11 | 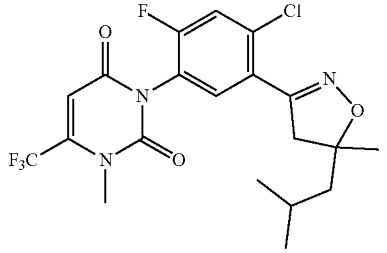 [SMILES: CC(C)CC1(C)CC(c2cc(-n3c(=O)cc(C(F)(F)F)n(C)c3=O)c(F)cc2Cl)=NO1] | 0.97 (3H, d), 1.00 (3H, d), 1.41 (3H, d), 1.64 (1H, m), 1.75 (1H, m), 1.83 (1H, m), 3.18 (1H, m), 3.31 (1H, m), 3.56 (3H, s), 6.36 (1H, s), 7.34 (1H, d), 7.64 (1H, dd) | 81.6% | 64.7% |

In addition, different substituents of raw materials are changed in the formula and according to the records of the preparation process, formula I compounds shown by different substituents can also be obtained, which also shows the universality of application of the method of the present invention.

The invention claimed is:

1. A synthesis method of a phenylisoxazoline compound, comprising:

1) reacting 2-fluoro-4-chloro-5-methylaniline (I) and a chloroformate compound to obtain a carbamate compound (II);

2) reacting the carbamate compound (II) with 3-amino-4,4,4-trifluorocrotonate, followed by methylation with a methylating reagent to obtain uracil (III);

3) processing uracil (III) by oxidization or dihalogenation hydrolysis to obtain uracil benzaldehyde (IV);

4) reacting the uracil benzaldehyde (IV) with hydroxylamine hydrochloride to obtain uracil benzaldoxime (V); and 5) conducting N-chlorosuccinimide (NCS) chlorination on the uracil benzaldoxime (V), followed by cyclization with an alkene compound (VI) to obtain the phenylisoxazoline compound (VII),

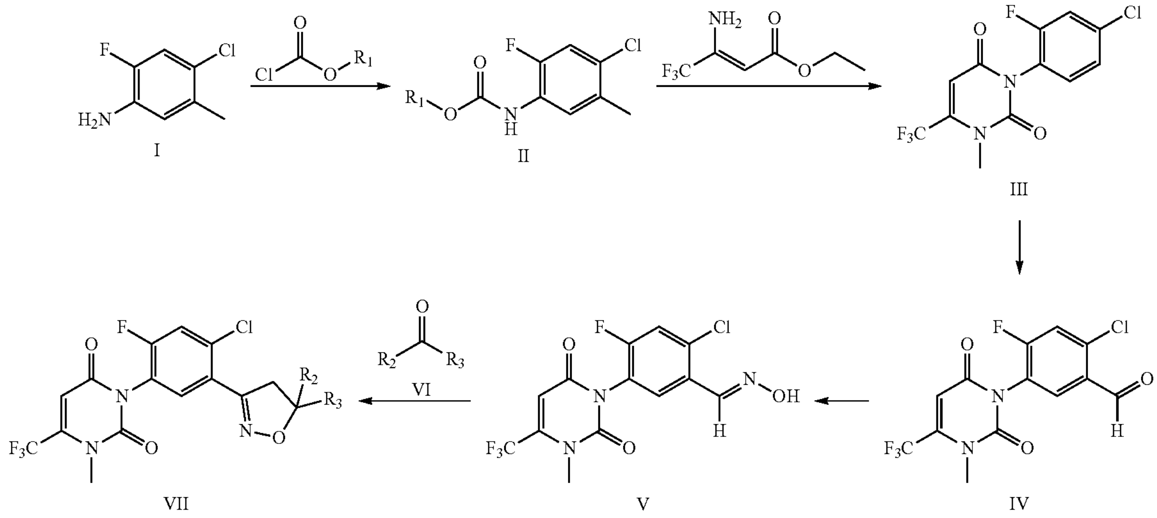

wherein, $R_1$ is methyl, ethyl, phenyl, 4-nitrophenyl, or benzyl;

$R_2$ is hydrogen, $C_1$-$C_4$ alkyl, $CO_2R_4$, or $CH_2ORs$;

$R_3$ is hydrogen, cyano, $C_1$-$C_4$ alkyl, $C_1$-$C_4$ haloalkyl, $CO_2R_4$, or $CH_2OR_5$;

$R_4$ is selected from hydrogen, $C_1$-$C_4$ alkyl, $C_1$-$C_4$ haloalkyl, $C_3$-$C_4$ alkenyl, $C_3$-$C_4$ alkyl, $C_1$-$C_4$alkoxy $C_1$-$C_4$ alkyl, $C_1$-$C_4$ alkylcarbonyl oxy $C_2$-$C_3$ alkyl, unsubstituted benzyl, unsubstituted furan methylene, unsubstituted tetrahydrofuran methylene, substituted benzyl, substituted furan methylene, and substituted tetrahydrofuran methylene that are substituted by 1-4 substituents independently selected from halogen, CN, $NO_2$, $C_1$-$C_4$ alkyl, and $C_1$-$C_4$ haloalkyl; and $R_5$ is selected from hydrogen, $C_1$-$C_4$ alkyl, $C_1$-$C_4$ haloalkyl, $C_1$-$C_4$ alkoxy carbonyl, $C_1$-$C_4$ alkyl carbonyl, $C_1$-$C_4$ haloalkyl carbonyl, $C_3$-$C_6$ cycloalkyl carbonyl, $C_3$-$C_6$ halocycloalkyl carbonyl, $C_1$-$C_4$ alkyl sulfonyl, $C_1$-$C_4$ halo alkyl sulfonyl, $C_1$-$C_3$ alkyl aminosulfonyl, di($C_1$-$C_3$) alkyl aminosulfonyl, $C_1$-$C_3$ alkyl aminocarbonyl, di($C_1$-$C_3$) alkyl aminocarbonyl, di($C_1$-$C_3$)alkyl aminothiocarbonyl, $C_1$-$C_2$ alkylsulfuryl $C_2$-$C_4$ alkyl carbonyl, phenyl $C_1$-$C_2$ alkyl, phenyl carbonyl, phenyl $C_1$-$C_2$ alkyl carbonyl, phenyl $C_2$-$C_4$ alkyl carbonyl, phenoxy $C_1$-$C_2$ alkyl carbonyl, thiophenyl carbonyl, pyrazole carbonyl, and quinoline carbonyl, which are unsubstituted or substituted by 1-4 substituents independently selected from the group consisting of halogen, CN, $NO_2$, $C_1$-$C_4$ alkyl, $C_1$-$C_4$ haloalkyl, $C_1$-$C_4$ alkoxy, $C_1$-$C_4$ haloalkoxy, $C_1$-$C_4$ alkoxy carbonyl, $C_1$-$C_4$ alkyl, $C_1$-$C_4$ alkyl sulfonyl, and phenoxy which is independently substituted by 1-4 halogens, CN, $NO_2$, $C_1$-$C_4$ alkyl, $C_1$-$C_4$ haloalkyl, $C_1$-$C_4$ alkoxy or $C_1$-$C_4$ haloalkoxy.

2. The synthesis method of the phenylisoxazoline compound according to claim 1, wherein in step 1), 2-fluoro-4-chloro-5-methylaniline (I) is heated to 60-100° C. in a solvent comprising an alkali, and the chloroformate compound is dropwise added to react for 1-4 h to produce the carbamate compound (II), wherein the molar ratio of 2-fluoro-4-chloro-5-methylaniline (I), the alkali, and the chloroformate compound is 1:(1-4):(1-2).

3. The synthesis method of the phenylisoxazoline compound according to claim 1, wherein in step 2), the carbamate compound (II) reacts with 3-amino-4,4,4-trifluorocrotonate in a solvent comprising a catalyst at 100-140° C. for 3-8 hours; cooling the resulting reaction mixture to room temperature, a methylation reagent and an alkali are added to react at 20-80° C. for 2-8 hours to obtain the uracil (III); and wherein the molar ratio of the carbamate (II), the 3-amino-4,4,4-trifluorocrotonate, the alkali, the catalyst, and the methylation reagent is 1:(1-1.2):(1.5-3):(0.01-0.1):(1-2).

4. The synthesis method of the phenylisoxazoline compound according to claim 1, wherein in step 3), the uracil (III), a halogenated reagent, a solvent and a catalyst are mixed to react at 50-150° C. for 2-10 hours; cooling the resulting reaction mixture to room temperature, and collecting an organic phase by extraction; and vacuum distilling the original phase to obtain dihalide; adding an acid to the dihalide for hydrolysis at 50-100° C. for 4-12 hours to obtain the uracil benzaldehyde (IV); and wherein the molar ratio of the uracil (III), the halogenated reagent, the catalyst, and the acid is 1:(2.5-3.5):(0.01-0.1):(10-30).

5. The synthesis method of the phenylisoxazoline compound according to claim 1, wherein in step 4), the uracil benzaldehyde (IV) reacts with hydroxylamine hydrochloride in alcohol at room temperature for 1-6 hours to obtain uracil benzaldoxime (V), wherein the molar ratio of the uracil benzaldehyde (IV) to hydroxylamine hydrochloride is 1:(1-1.5).

6. The synthesis method of the phenylisoxazoline compound according to claim 1, wherein in step 5), reacting the uracil benzaldoxime (V) and a halogenated reagent at 20-40° C. for 1-2 hours; cooling the resulting reaction mixture to 0-15° C., and then adding the alkene compound (VI) and an alkali to react for 1-4 hours to obtain the phenylisoxazoline compound (VII);

wherein the molar ratio of the uracil benzaldoxime (V), the halogenated reagent, the alkene compound (VI), and the alkali is 1:(1-1.5): 1:(1-2).

7. An intermediate compound for synthesizing a phenylisoxazoline compound, having a structural formula V of claim 1.

8. A synthesis method of a phenylisoxazoline compound, comprising:

chlorinating uracil benzaldoxime (V) using N-chlorosuccinimide (NCS) to obtain the compound of formula V; and cyclization with the compound of formula V with an alkene compound (VI) to obtain the phenylisoxazoline compound (VII):

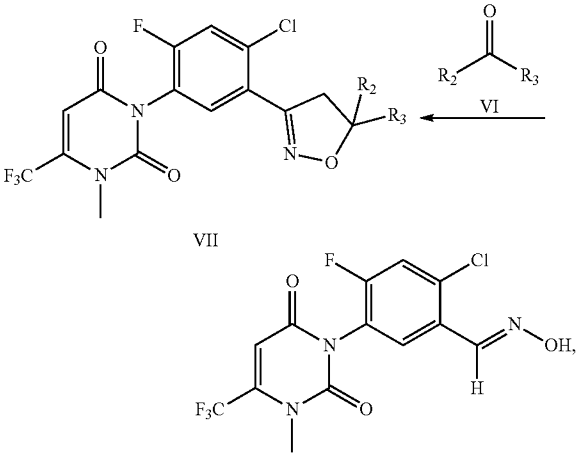

VII

V wherein, $R_2$ is hydrogen, $C_1$-$C_4$ alkyl, $CO_2R_4$, or $CH_2OR_5$;

$R_3$ is hydrogen, cyano, $C_1$-$C_4$ alkyl, $C_1$-$C_4$ haloalkyl, $CO_2R_4$, or $CH_2OR_5$;

$R_4$ is selected from hydrogen, $C_1$-$C_4$ alkyl, $C_1$-$C_4$ haloalkyl, $C_3$-$C_4$ alkenyl, $C_3$-$C_4$ alkyl, $C_1$-$C_4$alkoxy $C_1$-$C_4$ alkyl, $C_1$-$C_4$ alkylcarbonyl oxy $C_2$-$C_3$ alkyl, unsubstituted benzyl, unsubstituted furan methylene, unsubstituted tetrahydrofuran methylene, substituted benzyl, substituted furan methylene, and substituted tetrahydrofuran methylene that are substituted by 1-4 substituents independently selected from halogen, CN, $NO_2$, $C_1$-$C_4$ alkyl, and $C_1$-$C_4$ haloalkyl; and $R_5$ is selected from hydrogen, $C_1$-$C_4$ alkyl, $C_1$-$C_4$ haloalkyl, $C_1$-$C_4$ alkoxy carbonyl, $C_1$-$C_4$ alkyl carbonyl, $C_1$-$C_4$ haloalkyl carbonyl, $C_3$-$C_6$ cycloalkyl carbonyl, $C_3$-$C_6$ halocycloalkyl carbonyl, $C_1$-$C_4$ alkyl sulfonyl, $C_1$-$C_4$ halo alkyl sulfonyl, $C_1$-$C_3$ alkyl aminosulfonyl, di($C_1$-$C_3$) alkyl aminosulfonyl, $C_1$-$C_3$ alkyl aminocarbonyl, di($C_1$-$C_3$) alkyl aminocarbonyl, di($C_1$-$C_3$)alkyl aminothiocarbonyl, $C_1$-$C_2$ alkylsulfuryl $C_2$-$C_4$ alkyl carbonyl, phenyl $C_1$-$C_2$ alkyl, phenyl carbonyl, phenyl $C_1$-$C_2$ alkyl carbonyl, phenyl $C_2$-$C_4$ alkyl carbonyl, phenoxy $C_1$-$C_2$ alkyl carbonyl, thiophenyl carbonyl, pyrazole carbonyl, and quinoline carbonyl, which are unsubstituted or substituted by 1-4 substituents independently selected from the group consisting of halogen, CN, $NO_2$, $C_1$-$C_4$ alkyl, $C_1$-$C_4$ haloalkyl, $C_1$-$C_4$ alkoxy, $C_1$-$C_4$ haloalkoxy, $C_1$-$C_4$ alkoxy carbonyl, $C_1$-$C_4$ alkyl, $C_1$-$C_4$ alkyl sulfonyl, and phenoxy which is independently substituted by 1-4 halogens, CN, $NO_2$, $C_1$-$C_4$ alkyl, $C_1$-$C_4$ haloalkyl, $C_1$-$C_4$ alkoxy or $C_1$-$C_4$ haloalkoxy.

* * * * *